United States Patent
Lecuyer et al.

(10) Patent No.: US 11,045,157 B2
(45) Date of Patent: *Jun. 29, 2021

(54) VISUAL INDICATOR FOR THE ASSESSMENT OF THE TILT OF THE FRANKFORT PLANE IN EXTRA ORAL DENTAL IMAGING DEVICES

(71) Applicant: TROPHY, Croissy-Beaubourg (FR)

(72) Inventors: Yann Lecuyer, Paris (FR); Olivier Martino, Marne la Vallee (FR)

( * ) Notice: Subject to any disclaimer, the term of this patent is extended or adjusted under 35 U.S.C. 154(b) by 174 days.

This patent is subject to a terminal disclaimer.

(21) Appl. No.: 15/532,213

(22) PCT Filed: Dec. 4, 2014

(86) PCT No.: PCT/IB2014/002981
§ 371 (c)(1),
(2) Date: Jun. 1, 2017

(87) PCT Pub. No.: WO2016/087894
PCT Pub. Date: Jun. 9, 2016

(65) Prior Publication Data
US 2018/0263579 A1    Sep. 20, 2018

(51) Int. Cl.
| | | |
|---|---|---|
| *A61B 6/14* | (2006.01) | |
| *A61B 6/03* | (2006.01) | |
| *A61B 6/04* | (2006.01) | |

(52) U.S. Cl.
CPC ............ *A61B 6/14* (2013.01); *A61B 6/032* (2013.01); *A61B 6/0428* (2013.01); *A61B 6/0492* (2013.01)

(58) Field of Classification Search
CPC .. A61B 6/03; A61B 6/032; A61B 6/04; A61B 6/0492; A61B 6/14; A61B 6/587; A61B 6/44

USPC ..................................... 378/38, 39, 40, 208
See application file for complete search history.

(56) References Cited

U.S. PATENT DOCUMENTS

| | | | |
|---|---|---|---|
| 2,264,410 | A | 12/1941 | Schier |
| 4,088,893 | A | 5/1978 | Schroeder |
| 5,511,106 | A | 4/1996 | Doebert |
| 6,052,428 | A | 4/2000 | Nakano |
| 6,863,440 | B2 | 3/2005 | Sildve |
| 7,469,032 | B2 | 12/2008 | Walker |
| 9,265,466 | B2 * | 2/2016 | Hirabayashi ......... A61B 6/0492 |
| 9,642,582 | B2 | 5/2017 | Lecuyer |

(Continued)

FOREIGN PATENT DOCUMENTS

| | | |
|---|---|---|
| JP | 2014/138692 | 7/2014 |
| WO | 2013/014488 | 1/2013 |

OTHER PUBLICATIONS

International Search Report, dated Aug. 7, 2015 International Application No. PCT/IB2014/002981, 4 pages.

*Primary Examiner* — Jurie Yun

(57) ABSTRACT

A patient positioning apparatus for an extra-oral imaging system that includes a support base adjustable in at least one dimension and a cephalometric module coupled to the support base and configured to position a cephalometric imaging sensor about an imaging area formed with an x-ray source, where x-rays from the x-ray source impinge the cephalometric sensor after radiating the imaging area. A patient positioning unit is positioned operatively near the imaging area, and a retractable Frankfort plane positioning indicator and methods for using the same are provided.

15 Claims, 13 Drawing Sheets

(56) References Cited

U.S. PATENT DOCUMENTS 9,743,893 B2 * 8/2017 Inglese .................... A61B 6/14
10,405,816 B2 * 9/2019 Congy .................... A61B 6/06

* cited by examiner

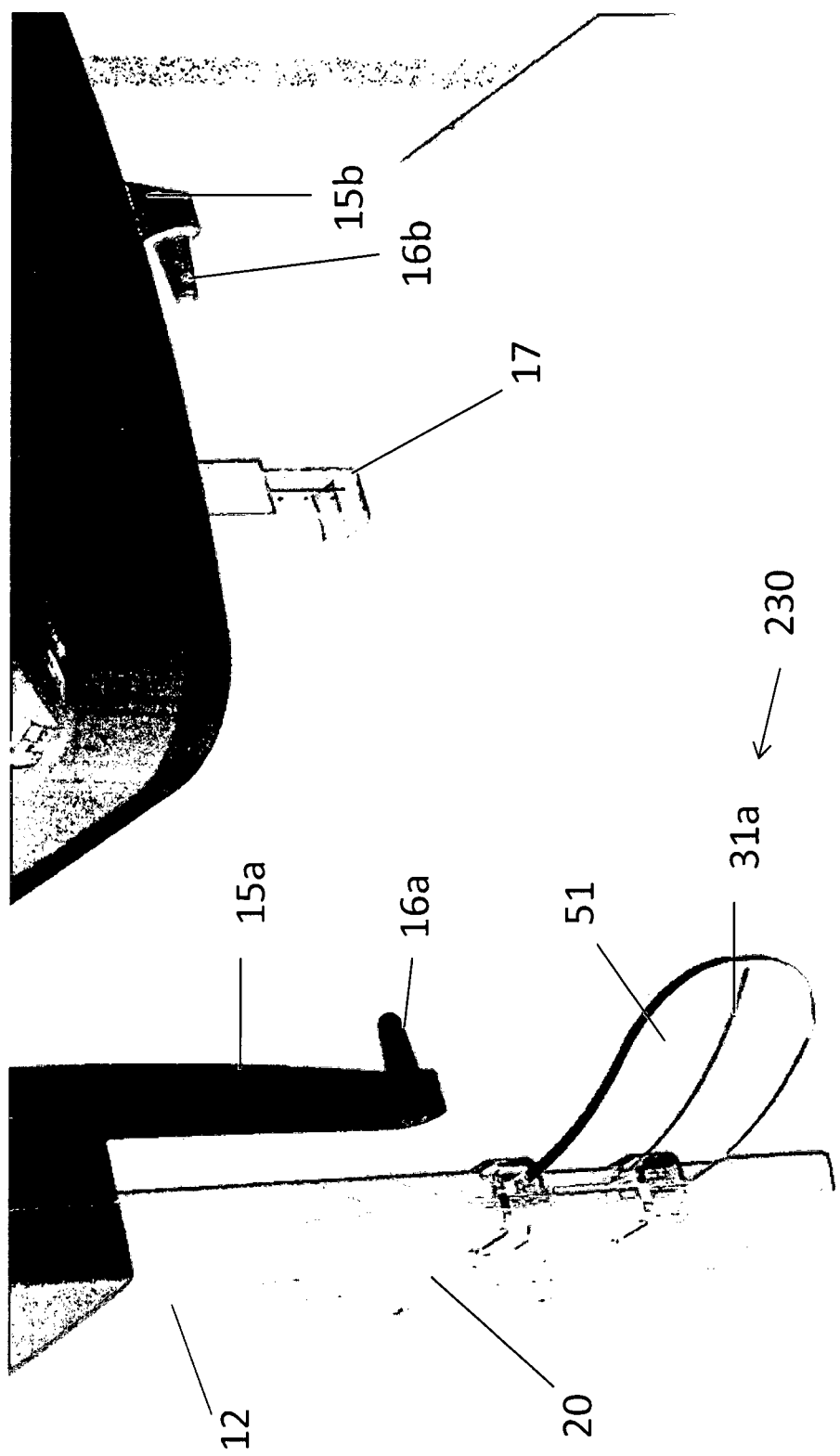

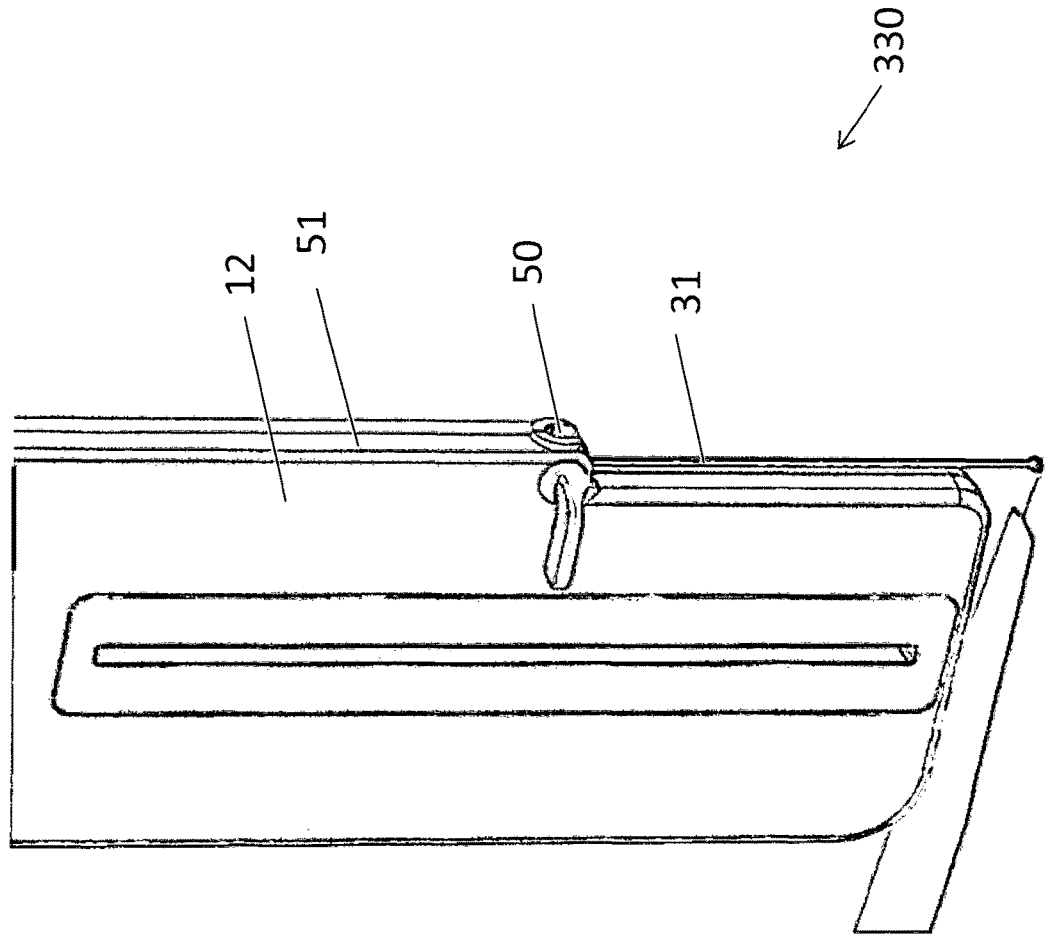

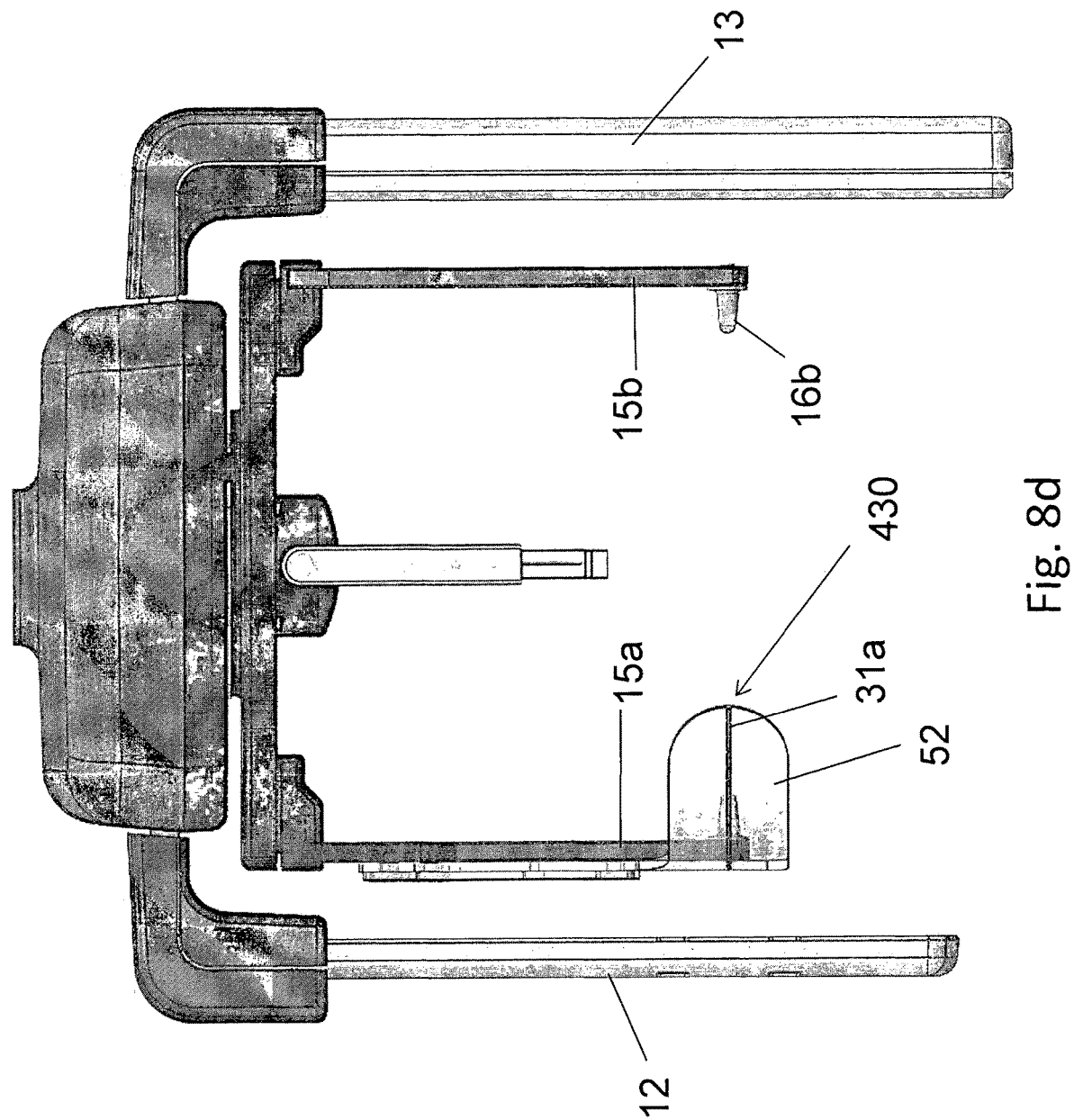

VISUAL INDICATOR FOR THE ASSESSMENT OF THE TILT OF THE FRANKFORT PLANE IN EXTRA ORAL DENTAL IMAGING DEVICES

CROSS REFERENCE TO RELATED APPLICATIONS

This application claims the benefit of and is a U.S. National Phase filing of PCT Application PCT/IB2014/002981 filed Dec. 4, 2014, entitled "VISUAL INDICATOR FOR THE ASSESSMENT OF THE TILT OF THE FRANKFORT PLANE IN EXTRA ORAL DENTAL IMAGING DEVICES", in the name of Lecuyer et al. which is incorporated herein by reference in their entirety.

FIELD OF THE INVENTION

The invention relates generally to the field of dental x-ray imaging, and more particularly, to imaging in a cephalometric x-ray mode for dental applications. Further, the invention relates to a combined cephalometric, panoramic and computed tomography dental imaging apparatus and/or methods.

BACKGROUND

Dental panoramic and cephalometric x-ray imaging scans offer the possibility to access information of the internal structure of teeth and to a patient's mouth anatomy. A panoramic imaging device can include a vertical column supporting a horizontal arm at an adjustable height. The horizontal arm supports a rotatable gantry with an x-ray source and digital sensor usually having the shape of a vertical slot facing each other at both sides of the gantry. During a panoramic scan, the gantry carries out a combined movement of rotation about its axis and translation. In the final reconstructed panoramic image, the teeth and anatomical structures are sharp inside an area named the focal trough while the anatomical structures outside the focal trough are blurred.

The general cephalometric imaging device is different. In most of the cases, the sensor is positioned at the extremity of a long arm and is positioned at a distance about 1.7 meters away from the source. The necessity to have the sensor positioned far away from the source originates from the necessity to have an approximately equal magnitude factor for every part of the patient's skull. The imaging process may consist in one single shot of the patient's skull with the x-ray beam impinging a full (e.g., square) sensor after radiating the patient. As an alternative to decrease the size of the sensor, a linear elongated sensor can be used in association with a linearly elongated (e.g., vertical) slit-shaped collimator that aims at shaping the x-ray beam before the x-ray beam radiates the patient. The patient is positioned between the elongated collimator and the elongated sensor. A linear scan can be performed by horizontally translating a vertically elongated sensor and a vertically elongated collimator and changing the direction of the x-ray beam accordingly with a primary collimator positioned in front of the X-ray source. The images collected during the scan are merged together to form a projection of the patient's skull. In the cephalometric or skull imaging technique, the patient can be positioned facing the x-ray beam or in a profile position.

For both panoramic and cephalometric dental x-ray imaging, the quality of the resulting images depends, among other things, on the precise positioning of the patient's head relative to the x-ray beam. Especially, the Frankfort plane, which is defined as a reference line on the patient's face connecting the bottom of the eye-ball socket and the ear canal, has to be horizontal. If the Frankfort plane is tilted relative to the horizontal position during a panoramic scan, some anatomical structures such as the base of the incisors lie out of the focal trough and are blurred on the reconstructed panoramic image. In cephalometric imaging, a tilted Frankfort plane can result in the superimposition of structures like the mandibular jawbone and the spine, which then can contaminate the reconstructed panoramic image and/or complicate the diagnosis.

In U.S. Pat. Nos. 6,052,428 and 7,469,032, a horizontal light beam is projected on the patient's face and the practitioner has then to position the patient's head so that the projection of the beam coincides with the Frankfort plane defined above. The light source is conventionally a laser and is generally located near the x-ray source or on the frame of the vertical column, either in the embodiment of a panoramic imaging device or a cephalometric imaging device. Nevertheless, lasers are expensive and the use of one or several lasers increases the unitary cost of the imaging devices. Moreover, in the case of a cephalometric imaging device, the lasers or light source are remote from the patient who is positioned close to the sensor which hangs at the end of a long cephalometric arm. Consequently, a precise adjustment of the light beam relative to the patient's face may be cumbersome.

In the panoramic imaging process, the patient conventionally must grasp a support or handles to remain fixed and stationary positioned during the scan. In an attempt to decrease the cost of a panoramic imaging device, US Patent Publication no. 2014/0147803 proposed an embodiment free of light source or laser. A transparent plastic shield is provided with a patient's forehead support and a chin rest to position the patient and with handles to be grasped by the patient. A series of horizontal lines are formed on the transparent plastic shield, for example by a serigraphic process, just in front of the patient's face when he is positioned in the panoramic device. The practitioner can then use these visual line indicators as a reference and correct the tilt of the patient's head so that the Frankfort plane of the patient coincides with one of the horizontal lines. Nevertheless, in US Patent Publication no. 2014/0147803, the indicator is part of a multi-function shield. Moreover, in this last embodiment (US2014/0147803), the horizontal lines formed on the transparent plastic shield are located inside the x-ray beam during the scan and can consequently pollute the reconstructed image. Actually, the serigraphic lines may be seen on the image. A Frankfurt plan visual indicator that remains out of the x-ray beam during the whole imaging operation is needed.

For the sake of simplicity of manufacturing, some elements specifically dedicated to the visual indication of horizontal lines to assist the patient's positioning are needed. The technical solution proposed in U.S. Pat. No. 6,863,440 to assist the positioning of the head of the patient in a cephalometric imaging process consists in a slot made on each of the two ear rod supports used for holding the patient. The dentist looks through this slot and aligns the patient's head so that the Frankfort plane of the patient's head is aligned with this slot. But such an embodiment is neither satisfactory since the ear rod support around the slot is opaque, which hinders a correct observation of the patient's head by the practitioner. The consequence is that the practitioner has to apply an indicator mark such as an adhesive patch or a mark made of removable ink on the patient's face. This process is cumbersome and unpleasant for the patient.

There is still a need for a visual indicator that is inexpensive, laser-free, easy to manufacture, that can be outside the x-ray beam during the scan and/or does not hinder the visualization of the patient's head by the practitioner.

SUMMARY

An aspect of this application is to advance the art of medical digital radiography, particularly for dental applications.

Another aspect of this application is to address, in whole or in part, at least the foregoing and other deficiencies in the related art.

It is another aspect of this application to provide, in whole or in part, at least the advantages described herein.

An advantage offered by apparatus and/or method embodiments of the application relates to improved imaging of teeth, jaw and head features surfaces at a lower cost over conventional imaging methods.

An advantage offered by apparatus and/or method embodiments of the application relates to providing a visual indication of alignment between a Frankfort plane and cephalometric imaging apparatus or a patient positioning apparatus thereof.

An advantage offered by apparatus and/or method embodiments of the application relates to providing a visual indication of alignment between a Frankfort plane and for a cephalometric imaging apparatus.

According to one aspect of the disclosure, there is provided a method for positioning an extra-oral imaging system that can include positioning at least one first temporal holding member to indicate a first position of ear canals of a patient; positioning at least one second holding member to indicate a second position of a bottom of an eye-ball socket; moving a reciprocally positionable Frankfort plane indicator into a selected visually alignment by superimposing at least one horizontal marker of the Frankfort plane indicator in correspondence with the first position and the second position.

According to one aspect of the disclosure, there is provided an extra-oral imaging system that can include a support base adjustable in at least one dimension; a cephalometric module coupled to the support base and configured to position a cephalometric imaging sensor about a first imaging area formed with an x-ray source, where x-rays from the x-ray source impinge the cephalometric sensor after radiating the first imaging area; a cephalometric patient positioning unit positioned operatively near the first imaging area; and a retractable cephalometric Frankfort plane positioning indicator.

These objects are given only by way of illustrative example, and such objects may be exemplary of one or more embodiments of the invention. Other desirable objectives and advantages inherently achieved by the may occur or become apparent to those skilled in the art. The invention is defined by the appended claims.

BRIEF DESCRIPTION OF THE DRAWINGS

The foregoing and other objects, features, and advantages of the invention will be apparent from the following more particular description of the embodiments of the invention, as illustrated in the accompanying drawings.

The elements of the drawings are not necessarily to scale relative to each other. Some exaggeration may be necessary in order to emphasize basic structural relationships or principles of operation. Some conventional components that would be needed for implementation of the described embodiments, such as support components used for providing power, for packaging, and for mounting and protecting system optics, for example, are not shown in the drawings in order to simplify description.

FIG. 6 is a diagram that shows a perspective view of a cephalometric imaging unit with a Frankfort plane visual indicator according to a third exemplary embodiment of the application.

FIG. 7b is a diagram that shows a perspective view of a cephalometric imaging unit with a Frankfort plane visual indicator in a retracted position according to a fourth exemplary embodiment of the application.

FIGS. 8c-8d are diagrams that show a side view and a front view of a cephalometric imaging unit with a Frankfort plane visual indicator in an operative position according to a fifth exemplary embodiment of the application.

DESCRIPTION OF EXEMPLARY EMBODIMENTS

Figure 1:
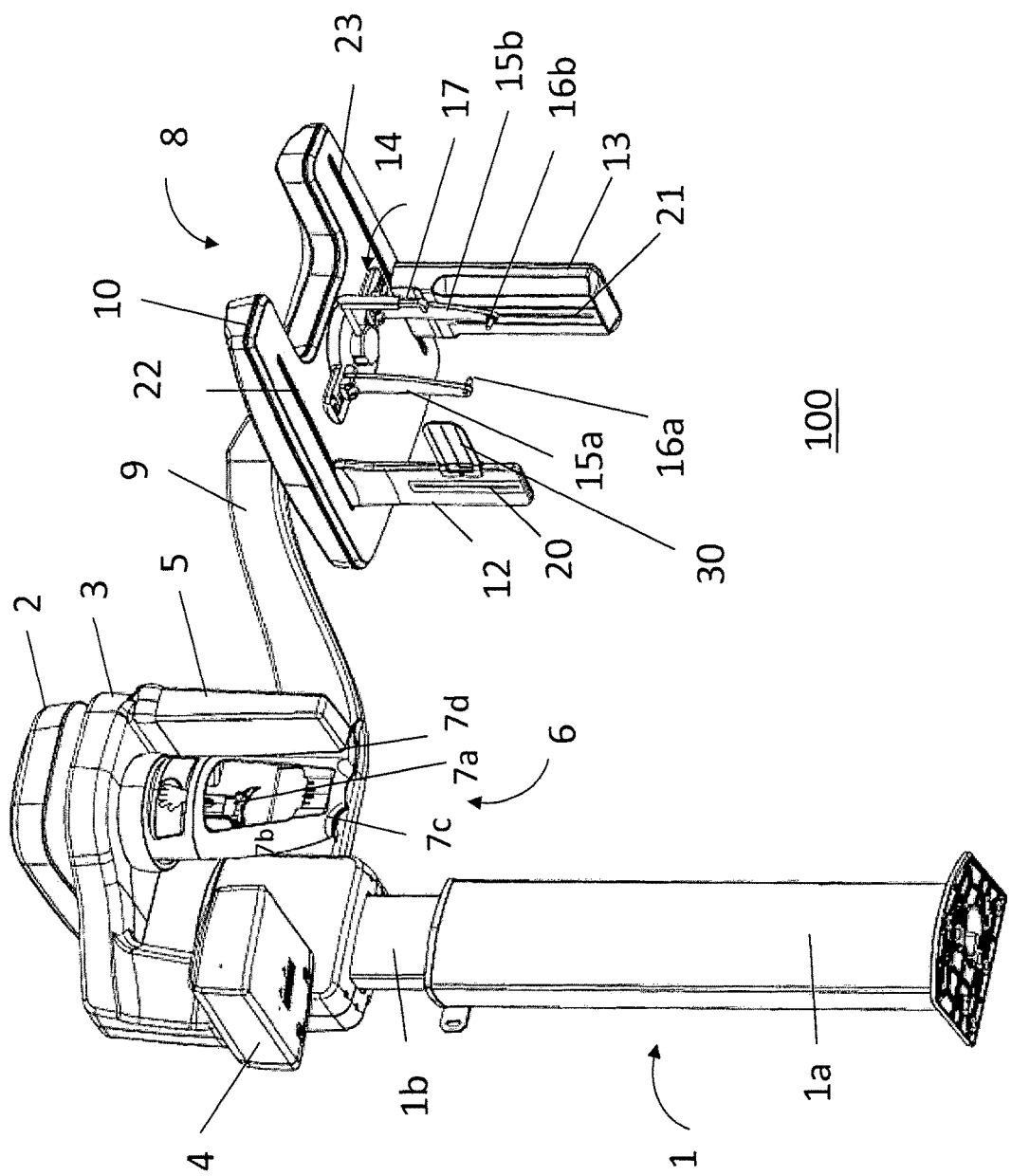
FIG. 1 is a diagram that shows a perspective view of an extra-oral dental imaging system including a cephalometric imaging unit with a Frankfort plane visual indicator according to a first exemplary embodiment of the application.

The following is a description of exemplary embodiments, reference being made to the drawings in which the same reference numerals identify the same elements of structure in each of the several figures.

Where they are used in the context of the present disclosure, the terms "first", "second", and so on, do not necessarily denote any ordinal, sequential, or priority relation, but are simply used to more clearly distinguish one step, element, or set of elements from another, unless specified otherwise.

As used herein, the term "energizable" relates to a device or set of components that perform an indicated function upon receiving power and, optionally, upon receiving an enabling signal. The term "actuable" has its conventional meaning, relating to a device or component that is capable of effecting an action in response to a stimulus, such as in response to an electrical signal, for example.

FIG. 1 is a diagram that shows a perspective view of an extra-oral dental imaging system including a cephalometric imaging unit with a Frankfort plane visual indicator according to a first exemplary embodiment of the application. As shown in FIG. 1, an exemplary extra-oral dental imaging system 100 includes a support structure that can include a support column 1. The column 1 may be adjustable in two-dimensions or three-dimensions. For example, the column 1 can be telescopic and may include an upper part 1b sliding inside a lower part 1a. A horizontal mount 2 may be supported or held by the vertical column 1 and can support a rotatable gantry 3. An x-ray source 4 and a first x-ray imaging sensor 5 are attached or coupled to the gantry 3 in correspondence (e.g., opposite, aligned) to each other. The first x-ray sensor 5 may be a panoramic (e.g., slit-shaped) sensor or a Computerized Tomography (e.g., rectangular, square-shaped) sensor. Preferably, the x-ray beam originating from the x-ray source 4 impinges the sensor 5 after radiating a first imaging area or the patient. A first patient positioning and holding system 6 can be operatively positioned near or in the first imaging area. In one embodiment, the first patient positioning and holding system 6 may be between the x-ray source 4 and the first x-ray imaging sensor 5. The first patient positioning and holding system 6 can include a forehead support 7a and a shield 7b including two handles 7c and 7d. The patient can then grasp the handles 7c and 7d and remain motionless during the CT scan or panoramic scan.

Figure 2:
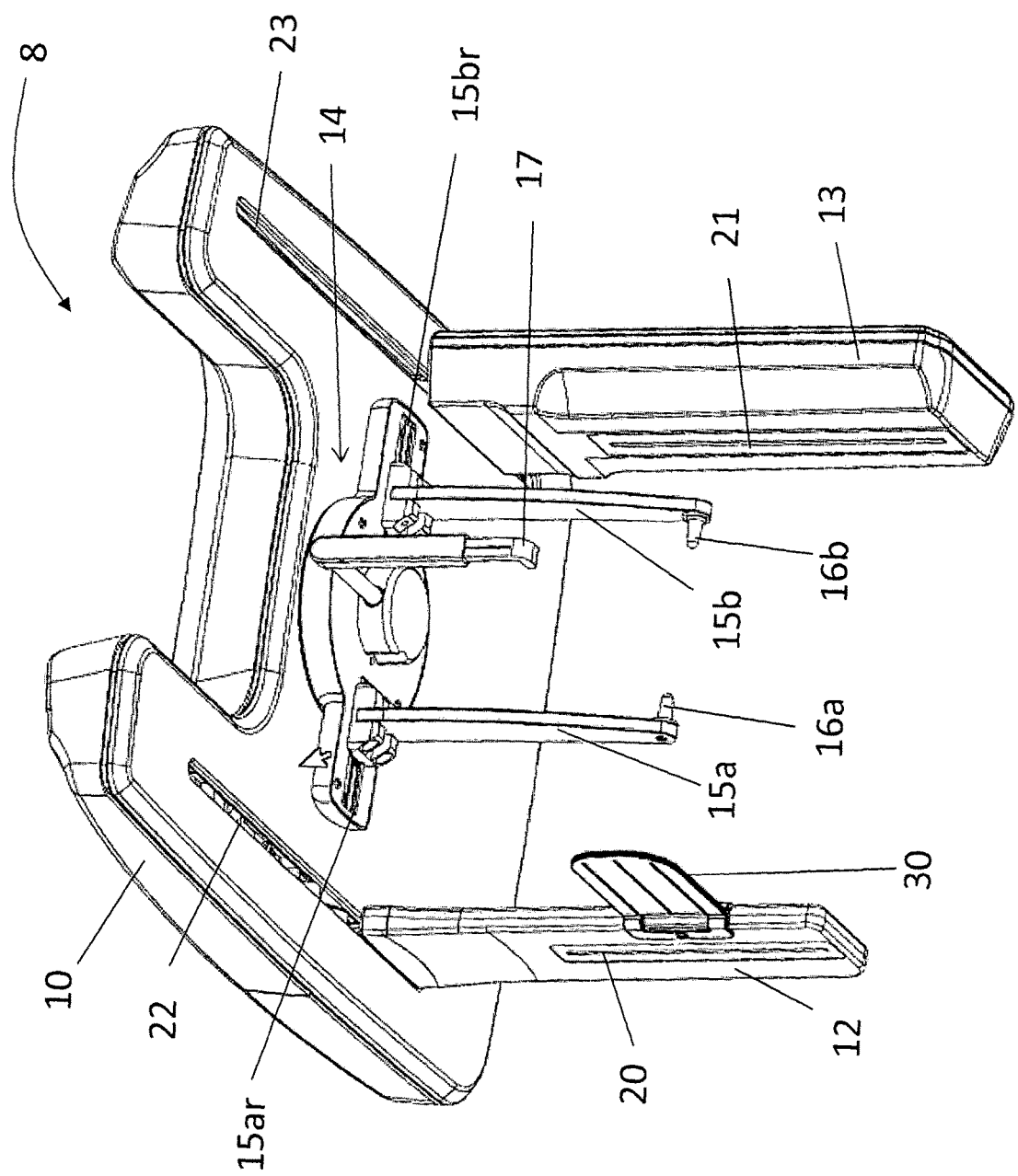
FIG. 2 is a diagram that shows a perspective view of a cephalometric imaging unit with a Frankfort plane visual indicator according to a first exemplary embodiment of the application.

More remote from the x-ray source 4, a cephalometric imaging unit 8 may be held in correspondence to the x-ray source 4. For example, as shown in FIG. 1, the cephalometric imaging unit 8 can be attached or coupled to the upper part 1b of the vertical column via an extended (e.g., horizontal) cephalometric arm 9. The cephalometric imaging unit 8 can include a mount 10 supporting a collimator 12, a second or cephalometric sensor 13 and a second patient positioning and holding system 14. As can also be seen in FIG. 2, the second patient positioning and holding system 14 can include a forehead support 17 and two temporal holding members 15a and 15b each supporting an ear rod 16a and 16b. Preferably, the x-ray beam originating from the x-ray source 4 impinges the sensor 13 after radiating a second or cephalometric imaging area or the patient. The second patient positioning and holding system 14 can be operatively positioned near or in the second imaging area. In one embodiment, thanks to the second patient positioning and holding system 14, the patient is precisely and repeatedly positioned between the collimator 12 and the sensor 13, preferably in the second imaging area. One or more of the holding members 15a and 15b can respectively slide along rails 15ar and 15br so that the distance between the two ear rods 16a and 16b can be changed to adjust to fit the patient's head. The forehead support 17 can also be adjustable. For example, the forehead support 17 can be adjustable in at least in two dimensions by sliding along the horizontal and vertical directions (see arrows A and B on FIG. 3). Alternatively, the forehead support 17 can be adjustable in three-dimensions around three or more axis.

Figure 3:
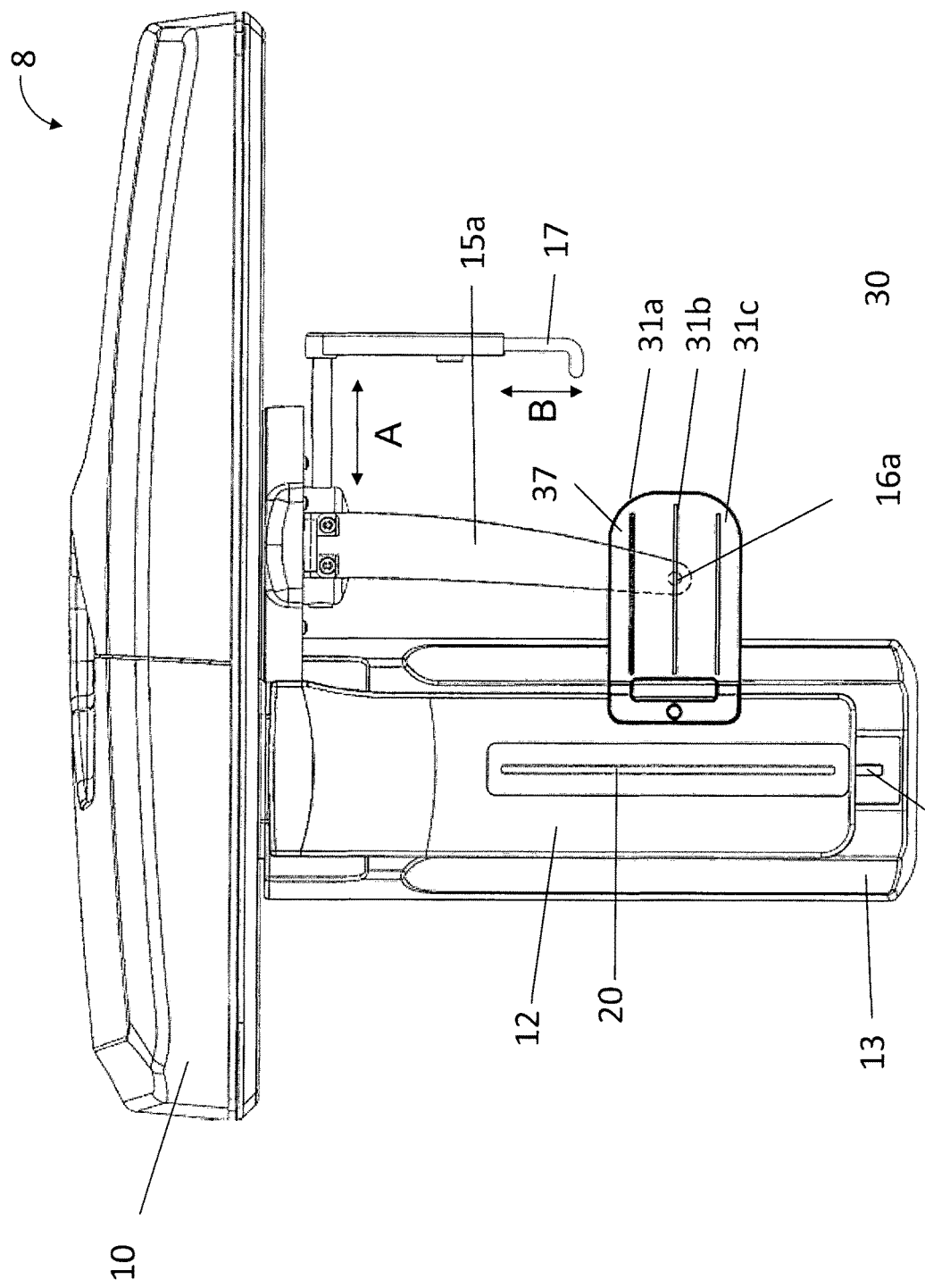
FIG. 3 is a diagram that shows a side view of a cephalometric imaging unit with a Frankfort plane visual indicator according to a first exemplary embodiment of the application.

FIG. 3 is a diagram that shows a side view of a cephalometric imaging unit with a Frankfort plane visual indicator according to the first exemplary embodiment of the application. As shown in FIG. 3, the collimator 12 can include an elongated opening or slit 20 to shape an x-ray beam. The x-ray sensor 13 can include an active area 21 having an elongated shape (e.g., a vertical slit) facing the vertical slit 20 of the collimator 12 (e.g., across the second imaging area). The sensor 13 and the collimator 12 face each other so that the sensor 13 can receive the x-ray originating from the x-ray source 4 after the x-ray beam was shaped by the collimator 12 and after the x-ray beam radiated the patient positioned and held on the second patient's positioning and holding system 14. For the scanning of the complete skull of the patient, both the collimator 12 can move or slide during the x-ray scan along a rail 22 and the sensor 13 can move or slide along the rail 23, both rails being coupled to the mount 10. As shown in FIG. 3, the rails 22, 23 are embodied on a lower face of the mount 10 of the cephalometric imaging unit 8. At any time during the cephalometric x-ray scan, an alignment may exist between a primary collimator in front of the source (not shown), the slit 20 of the collimator 12 and the active area of the sensor 13. Such x-ray alignment is disclosed, for example, in U.S. Pat. No. 5,511,106. At selected positions of the ensemble during the cephalometric scan, an x-ray digital image is obtained. At the end of the scan, an image reconstructing device (e.g., hardware, software and/or image processing) reconstructs the whole skull image on the basis of the plurality of images obtained during the cephalometric scan, for example using algorisms known to the person skilled in the art.

For a correct patient's positioning allowing a good image quality in the exemplary extra-oral dental imaging system 100, the Frankfort plane containing a straight line passing though the bottom of the eye socket and the ear canal must be horizontal. For the purpose of controlling that the Frankfort plane is horizontal, an at least partially transparent visual indicator 30 that can include a plate 37 with at least one horizontal line 31 thereon can be used. A material may be considered to be substantially transparent when it transmits at least about 50 percent of visible light, preferably more than about 80 percent, more preferably more than about 95 percent of visible light. As shown herein, the indicator 30 can be attached to a lateral edge of the collimator 12 (e.g., see FIG. 1). This embodiment presents the advantage that the visual indicator 30 remains out of the x-ray beam that is shaped by the collimator slit 20 during the whole scan. When the patient is positioned on the second patient positioning and holding system 14, the dentist can observe the Frankfort plane of the patient through the partially transparent indicator 30 and check that the head of the patient is accurately and correctly positioned, namely when the Frankfort plane coincides or at least is parallel with the at least one line of the visual indicator 30. In an exemplary embodiment, the visual indicator 30 can include a plurality of lines 31a, 31b, 31c regularly spaced at successive heights. Advantageously with this embodiment, the dentist refers to the line of the partially transparent indicator 30 that has the same vertical position as the Frankfort plane of the patient. Thus, a plurality of lines (e.g., lines 31a, 31b, 31c) can facilitate the head positioning of patients of various heights.

Figure 4:
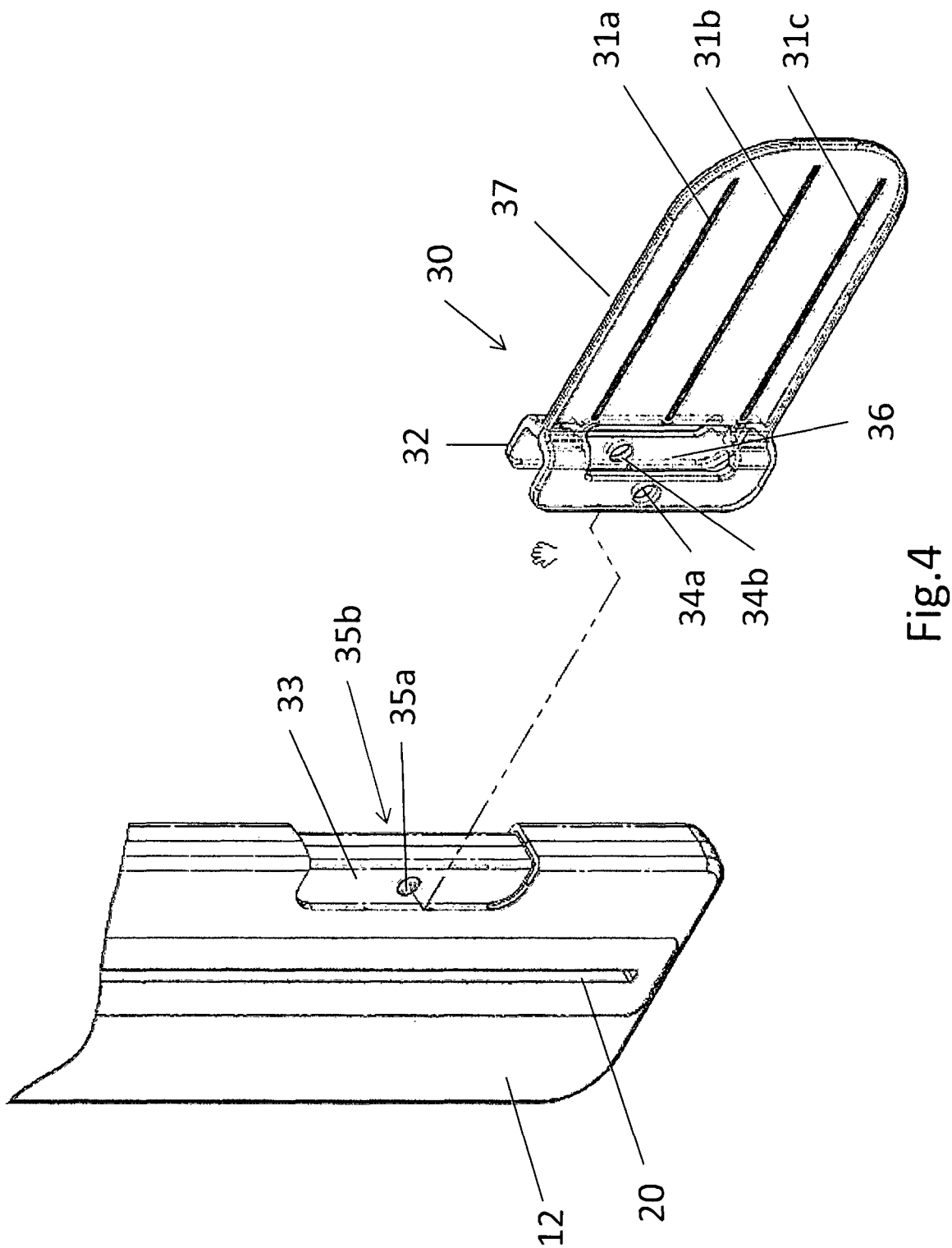
FIG. 4 is a diagram that shows exemplary cooperation of a collimator of a cephalometric imaging unit and a Frankfort plane visual indicator according to a first exemplary embodiment of the application.

FIG. 4 is a diagram that shows exemplary cooperation of a collimator of a cephalometric imaging unit and a Frankfort plane visual indicator according to the first exemplary embodiment of the application. As shown in FIG. 4, the visual indicator 30 may include of the first planar element 37 supporting at least one horizontal line 31a or a plurality of parallel lines (e.g., 31a, . . . , 31n). In one exemplary embodiment, the indicator 30 can be attached to the collimator 12. At one extremity of the planar element 37, an extension 32 having the shape of a horseshoe may be provided with two holes 34a and 34b. The collimator 12 is provided laterally with a recess 33 that extends across the width of the lateral face and partially on the front and rear face of the collimator 12. Two bosses 35a and 35b are positioned on the recess 33 at the front and rear surface of the collimator 12 symmetrically. The horseshoe shaped element 32 of the visual indicator 30 engages the recess 33 of the collimator 12 and the two bosses 35a and 35b engage the holes 34a and 34b. Thus, the holes 34a, 34b and the bosses 35a, 35b have corresponding shapes and/or dimensions. Preferably, the visual indicator 30 can be removably fixed on the lateral side of the collimator 12. Advantageously, an opening 36 can be formed on the horseshoe shaped element 32 to increase the resiliency of the element 32 and facilitate the engagement and disengagement of the element 32 with the recess 33 of the collimator 12. In an alternative embodiment, another recess is made on the opposite or other lateral side of the collimator, symmetrically with the illustrated recess 33, so that the visual indicator 30 can be fixed on either side of the collimator 12 for the convenience of the dentist.

Exemplary operations of the visual indicator 30 in the cephalometric imaging unit 8 will now be described. Before the patient enters inside the second patient positioning and holding system 14, the dentist enlarges the distance between both ear rods 16a and 16b. The patient positions his head between both temporal holding members 15a and 15b and then the holding members 15a and 15b are brought closer to each other so that the ear rods 16a and 16b gently penetrate the corresponding ear canals of the patient. At this step of the process of positioning the head, the patient can still rotate the head about the axis joining the ear canals. The dentist can then determine the accurate orientation of the patient head by superimposing the Frankfort plane of the patient's head and one of the at least one line 31a, 31b, 31c of the at least partially transparent visual indicator 30. Once the head is accurately positioned, the dentist optionally displaces the forehead support 17 by translation along both the axis A and B and positions the forehead support 17 against the patient's forehead or against the upper part of the patient's nose. The patient's head is thus oriented and/or fixed at the correct position and orientation of the Frankfort plane for cephalometric imaging using the visual indicator 30.

Figure 5:
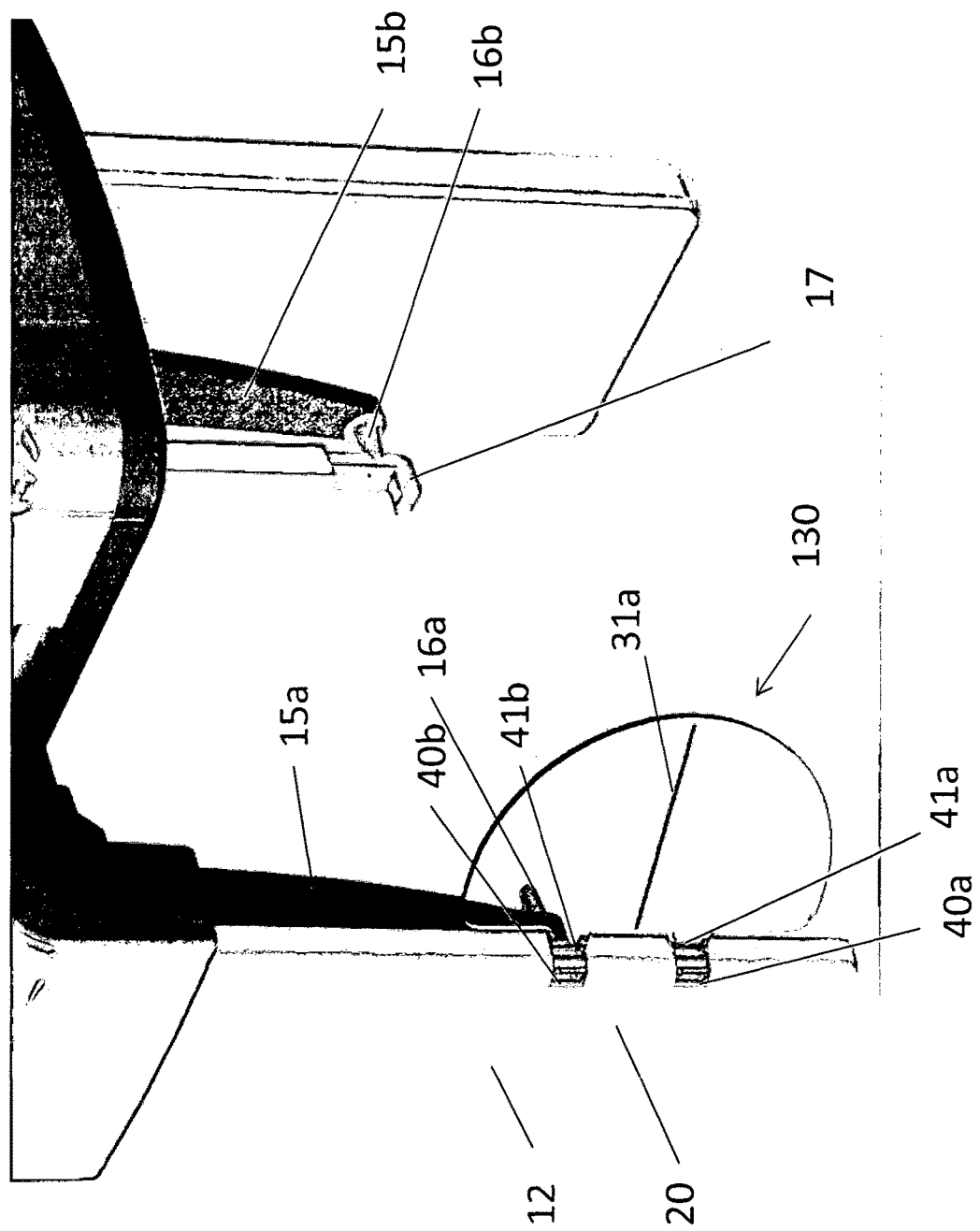
FIG. 5 is a diagram that shows a perspective view of a cephalometric imaging unit with a Frankfort plane visual indicator according to a second exemplary embodiment of the application.

FIG. 5 is a diagram that shows a dental cephalometric imaging unit with a second exemplary embodiment of a Frankfort plane visual indicator according to the application. As shown in FIG. 5, a Frankfort plane visual indicator 130 can be rotatably attached to collimator 12. In one embodiment, the collimator 12 may be provided with two notches 40a, 40b each provided with a hinge, and the visual indicator 130 may be provided with two protrusions 41a and 41b at a lateral extremity. A hole in each protrusion 41a and 41b may cooperate with each of the hinges. Advantageously, the visual indicator 130 can rotate about the hinge axis to be positioned closer to the patient's face when the visual indicator 130 is used. Thus, the visual indicator 130 may facilitate the assessment of the head's positioning by the dentist. In one exemplary embodiment, rotation by the visual indicator 130 away from the patient about the hinges is stopped from blocking or covering the vertical slit 20. It appears clearly that this second embodiment keeps the advantage of the first embodiment that the indicator linked on the collimator remains out of the x-ray beam and the does not pollute the reconstructed image.

FIG. 6 is a diagram that shows a dental cephalometric imaging unit with a third exemplary embodiment of a Frankfort plane visual indicator according to the application. As shown in FIG. 6, a shape of a Frankfort plane visual indicator 230 allows a horizontal line for guidance at a second or extended lateral side of the indicator 230 to be closer to the second imaging area than a first or adjacent lateral side of the indicator 230. In the third exemplary embodiment, the visual indicator 230 may again be attached to a lateral face of the collimator 12 and can include a curved shape. The extremity of the indicator 230 that extends away from the collimator 12 is curved towards the patient. Advantageously, the at least partially transparent visual indicator 230 and the at least one line 31a supported thereby are located closer to the patient. Alternatively, the indicator 230 may be sectioned, tiered or angled to approach the patient. In one exemplary embodiment, the visual indicator 230 can telescope out toward (and retract from) the patient. Further, the visual indicator 230 may be rotatably attached. Again, the visual indicator 230 is out of the x-ray beam during the whole of the scan. In one embodiment, a retractable cephalometric Frankfort plane positioning indicator can be rotatably mounted or formed with a distal end longitudinally spaced from a mounted end, where the distal end is closer to the first imaging area.

Figure 7A:
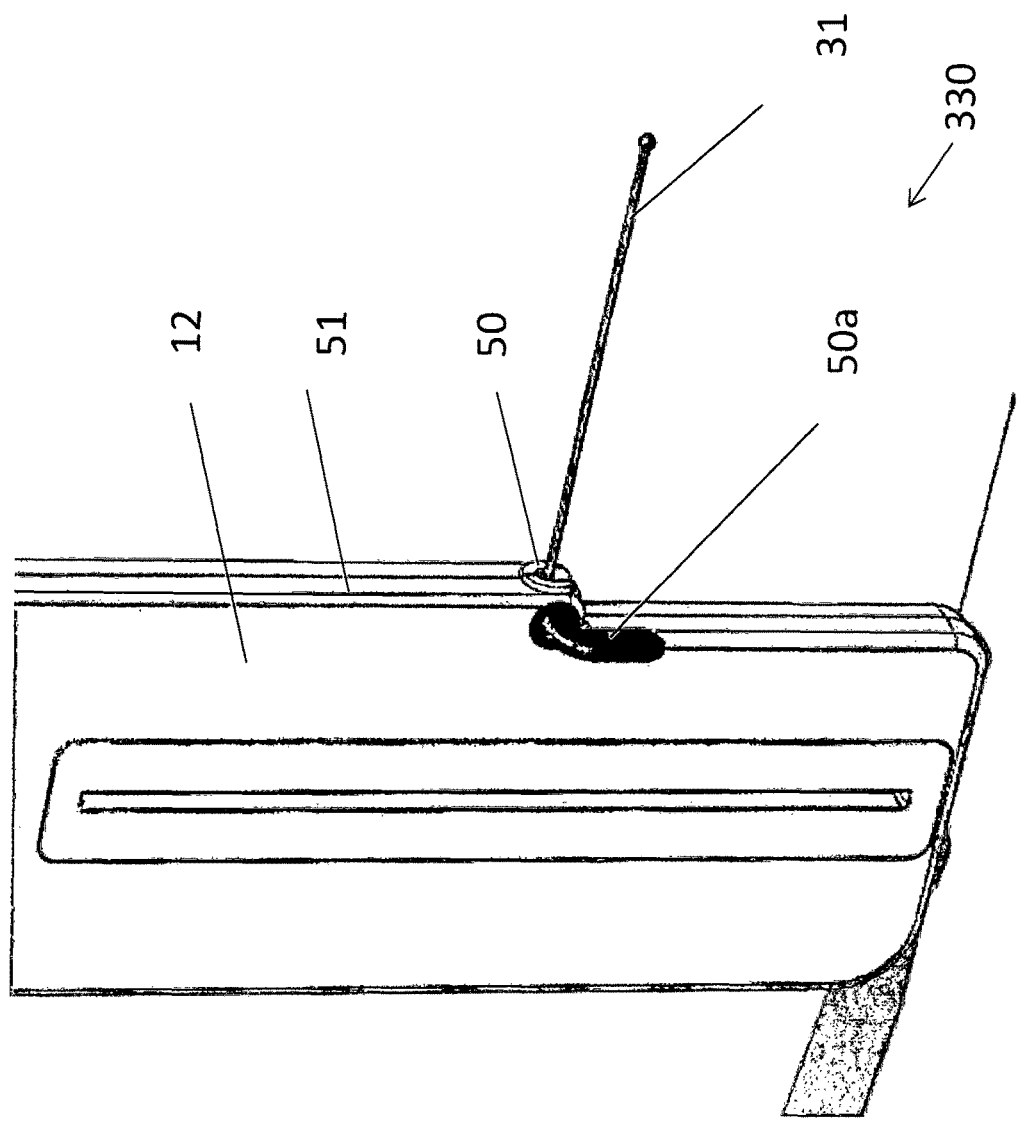
FIG. 7a is a diagram that shows a perspective view of a cephalometric imaging unit with a Frankfort plane visual indicator in an operative position according to a fourth exemplary embodiment of the application.

FIGS. 7a-7b are diagrams that show a dental cephalometric imaging unit with a fourth exemplary embodiment of a Frankfort plane visual indicator according to the application. As shown in FIGS. 7a-7b, a Frankfort plane visual indicator 330 can be an elongated unit that can be positioned in a horizontal orientation for guidance for the dentist in positioning. For a Frankfort plane visual indicator 330, a thin shaft 31 may be inserted in a housing 50 formed at (e.g., on a lateral face 51) of the collimator 12. The shaft 31 has the same functionality or role as the lines 31a, 31b and 31c of certain exemplary embodiments described herein. A horizontal position of the shaft 31 allows the dentist to compare the position of the Frankfort plane of the head of the patient with the horizontal orientation materialized by the shaft 31. By turning a lever 50a (e.g., in the clockwise direction), the user may reciprocally move (e.g., rotate) the shaft 31 from an operative position (or first position, FIG. 7a) to a retracted position (or second position, FIG. 7b) in which the shaft is within or within a profile (e.g., positioned vertically along the lateral face 51, within a contour or within a peripheral contour) of the collimator 12. Advantageously in the retracted position, the shaft 31 does not incur the risk of being bent, broken and possibly snatched from its housing 50. Further, in the retracted position, the shaft 31 has a reduced visual profile. In one exemplary embodiment, the shaft 31 can include a plurality of coupled shafts that unfold to be parallel in the operative position and fold back to a reduced profile in the retracted position. In one exemplary embodiment, the shaft 31 can be mounted on a portion of the cephalometric module and have a retracted position within a contour of a portion of the cephalometric module. In one embodiment, a cephalometric Frankfort plane positioning indicator can be mounted to the at least one temporal holding member and configured to reciprocally move between a first position corresponding to a portion of the at least one temporal holding member (e.g., ear rod) and a second retracted position.

It should be noted that in the exemplary embodiments described above, the visual indicator (e.g., visual indicator 30) is attached to the collimator and may remain out of the field of view during the whole x-ray scan while the collimator translates (e.g., laterally). Such exemplary embodiments advantageously insure that the visual indicator does not pollute the raw or processed image of the patient's head.

Figure 8A:
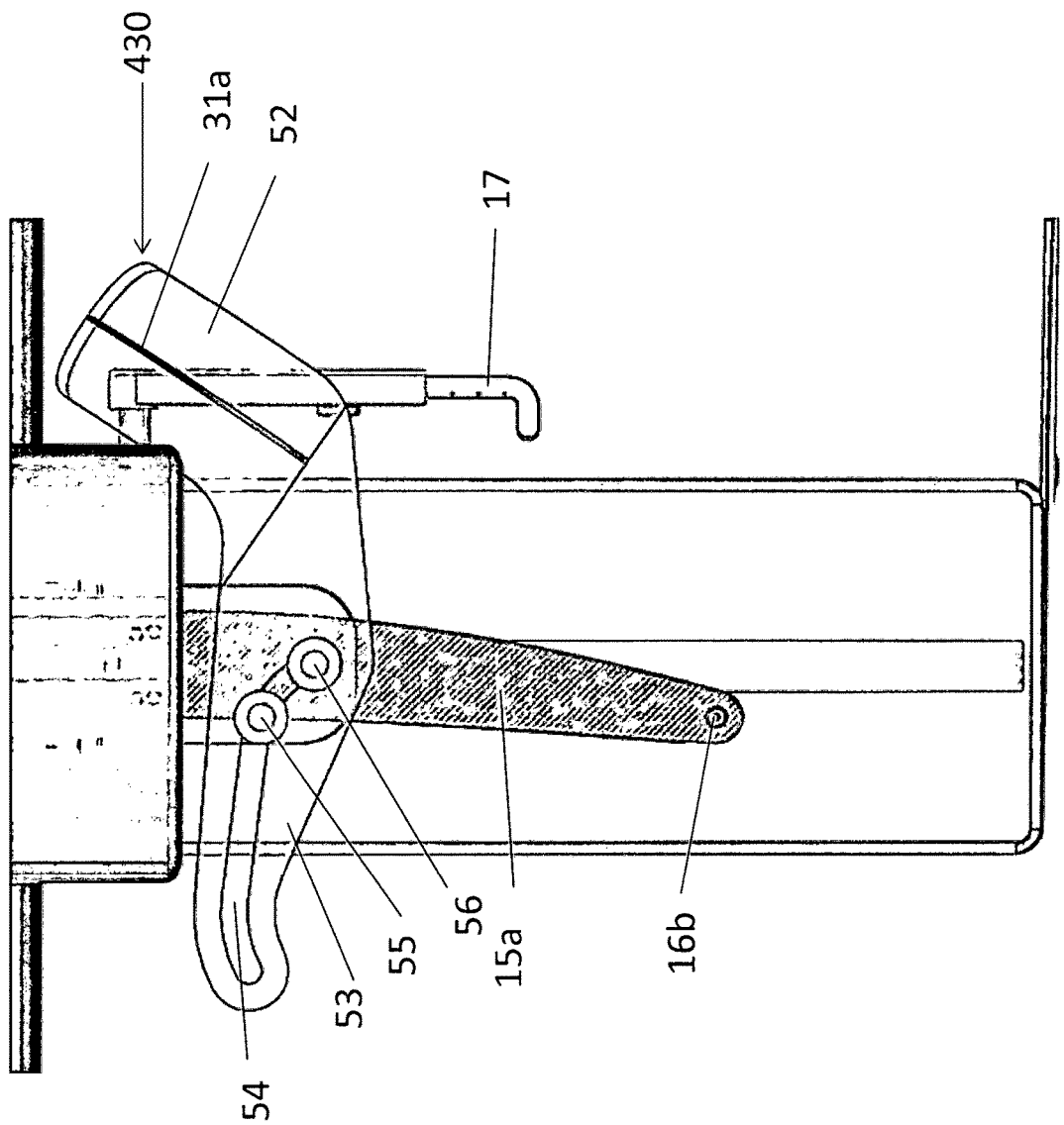
FIGS. 8a-8b are diagrams that show a side view and a perspective view of a cephalometric imaging unit with a Frankfort plane visual indicator in a retracted position according to a fifth exemplary embodiment of the application.
Figure 8B:
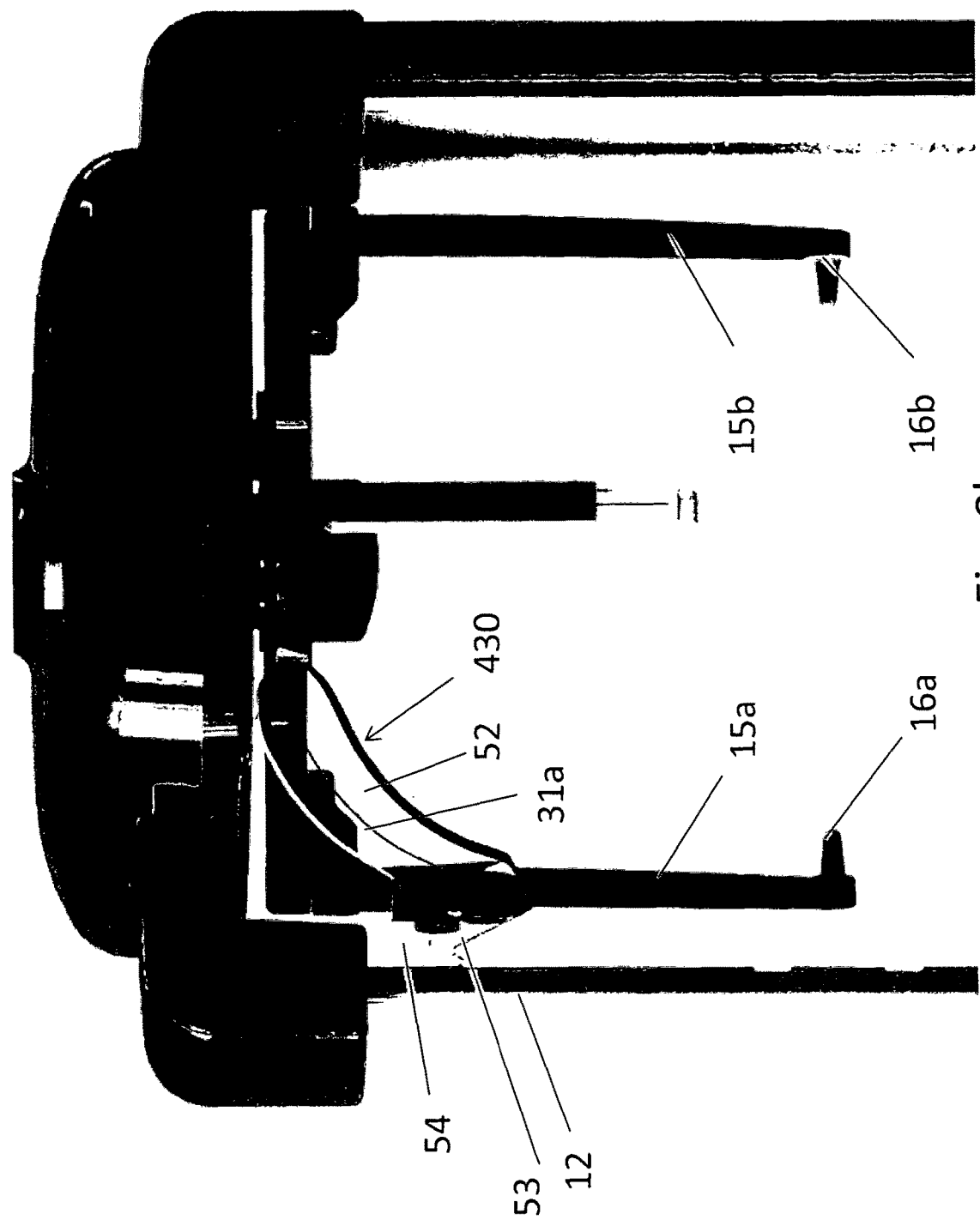

In certain alternative exemplary embodiments, a Frankfort plane visual indicator may be directly or indirectly supported by the mount 10 or other parts of the second patient positioning and holding system 14. FIGS. 8a-8b are diagrams that show a dental cephalometric imaging unit with a fifth exemplary embodiment of a Frankfort plane visual indicator according to the application. As shown in FIGS. 8a-8b, a Frankfort plane visual indicator 430 can be an elongated unit that can be reciprocally moved between a retracted position and a guidance position (e.g., in a horizontal orientation for guidance) for use by the dentist. In FIGS. 8a and 8b, the visual indicator 430 may be supported by one of the temporal holding members 15a. The visual indicator 430 can include a curved element 52 oriented toward the front side of the patient and a plane element 53 oriented toward the rear side of the patient. The curvature of the curved element 52 may be preferably directed towards the head of the patient, so that the at least one line 31a supported by the curved element 52 is positioned as close as possible to the head of the patient. A curved groove 54 may be formed on the plane element 53. Two extensions or engagement axis 55 and 56 protrude from a lateral face of one of the temporal holding members and penetrate the groove 54. The two axis 55 and 56 may guide a combined rotation-translational movement of the visual indicator 430 when the visual indicator 430 is reciprocally switched from the lower operative position in which the line 31a is horizontal and close to the patient's face to the retracted non-operative upper position as respectively represented on FIG. 8a and FIG. 8b. Advantageously in one exemplary embodiment, the dentist can retract the visual indicator 430 completely out of the field of view of the x-ray scan after the positioning of the patient's head. The visual indicator 430 then does not pollute the raw or processed x-ray image of the patient. Alternatively, in one exemplary embodiment, the visual indicator 430 is transparent to x-ray radiation needed for some or all dental imaging modalities.

Figure 8C:
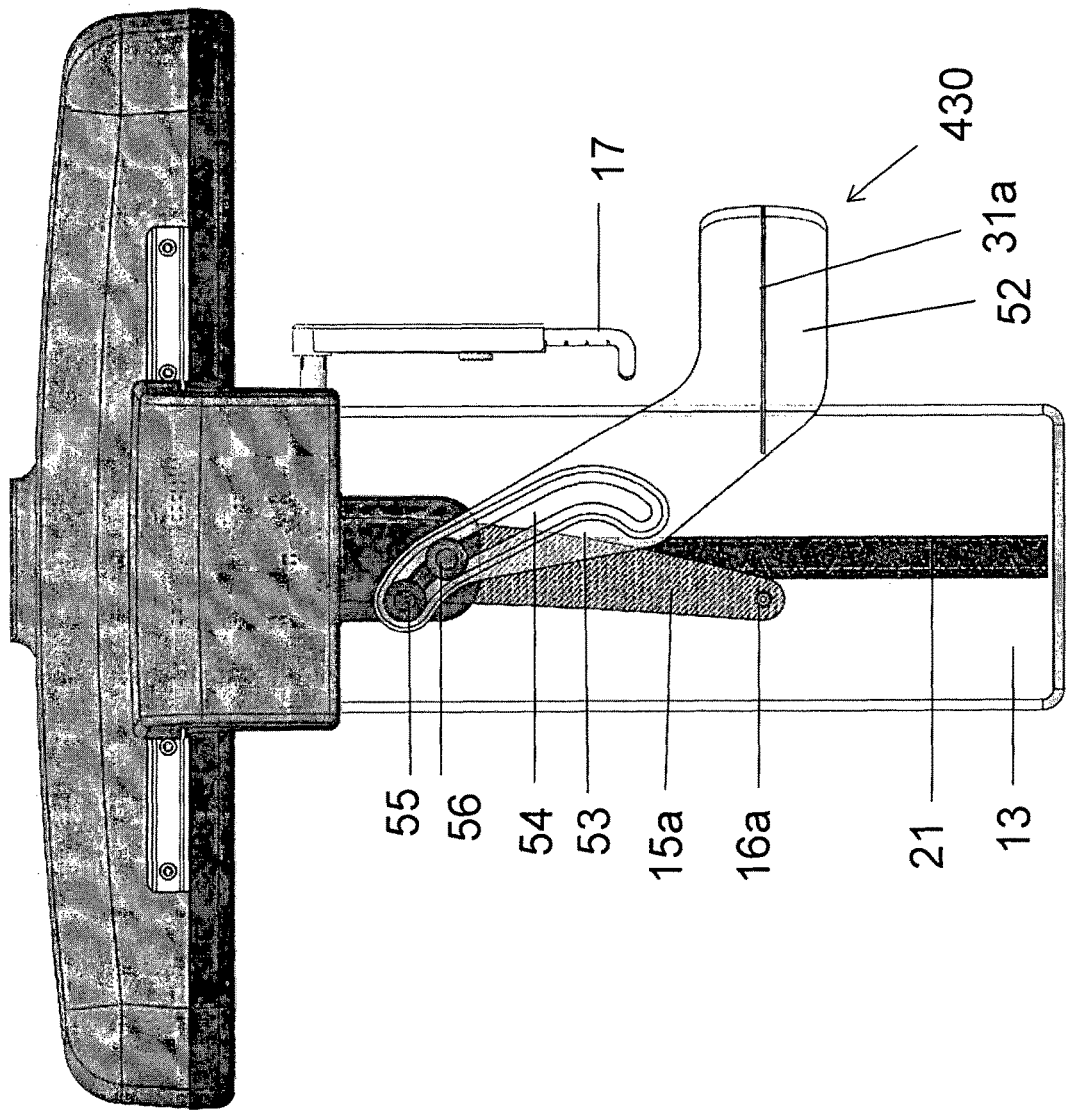

FIGS. 8c-8d are diagrams that show a side view and a front view of a cephalometric imaging unit with a Frankfort plane visual indicator in an operative position according to a fifth exemplary embodiment of the application.

Figure 9:
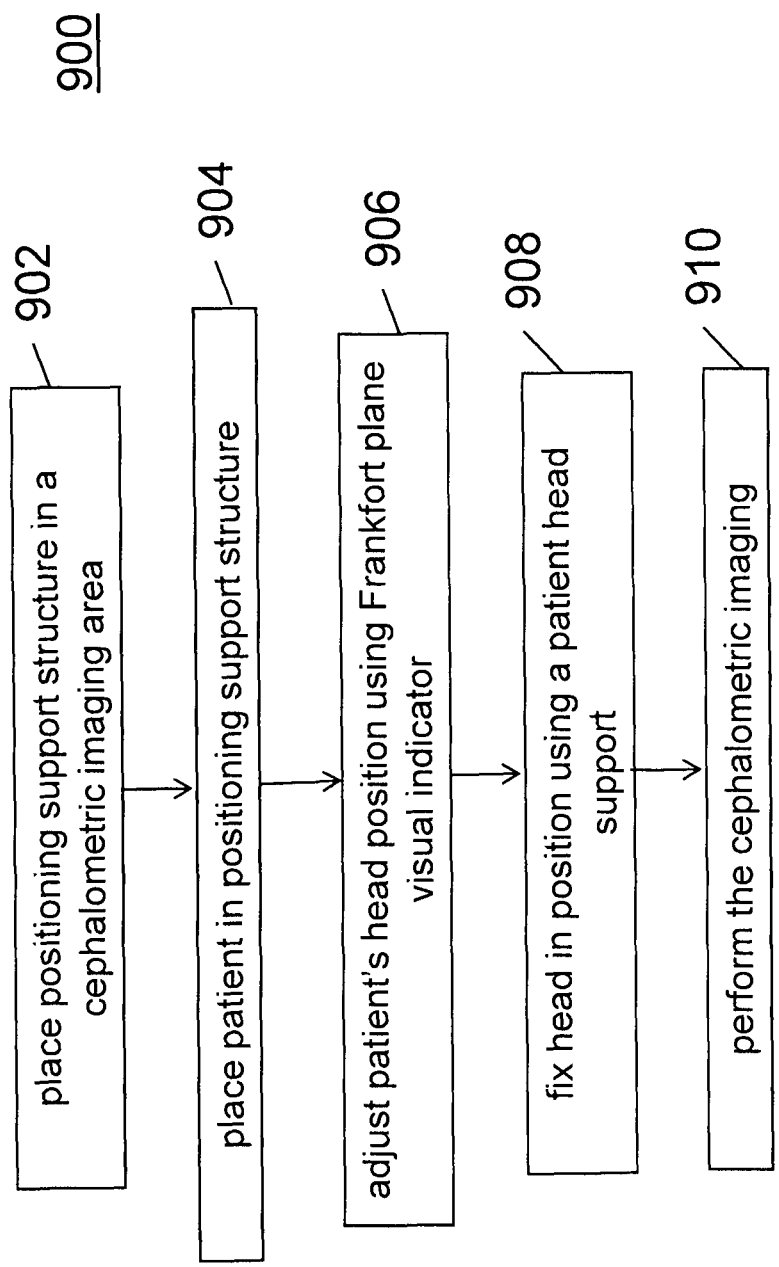
FIG. 9 is a flow chart that shows an exemplary method of generating a cephalometric image using a dental extra-oral system according to embodiments of the application.

Referring to FIG. 9, a flow chart that shows an exemplary method of generating a cephalometric image using a dental extra-oral system according to embodiments of the application will now be described. As shown in FIG. 9, the method can be implemented by embodiments of radiographic dental positioning support structures shown in FIGS. 1-8d; however, the method of FIG. 9 is not intended to be limited thereby.

As shown in FIG. 9, a positioning support structure can be attached to or part of a cephalometric imaging area of a dental extra-oral system (operation block 902). Then, a patient can be placed in the positioning support structure in the cephalometric imaging area system (operation block 904). For example, the patient can use the second patient positioning and holding system 14 described herein. Alternatively, the patient can use a different type of positioning device such as a chin rest type, a shield type or other conventional positioning devices. The dentist can determine the accurate orientation of the patient head by superimposing the Frankfort plane of the patient's head and a Frankfort plane visual indicator such as visual indicator 30, 130, 230, 330, 430 or the like (operation block 906). In one embodiment, the dentist can then determine the accurate orientation of the patient head by superimposing the Frankfort plane of the patient's head one of the at least one line 31a, 31b, 31c of the at least partially transparent visual indicator 30 suitably attached (e.g., indirectly or directly) to the collimator 12, mount 10, or sensor 13. Once the head is accurately positioned, the dentist optionally locks the patient in place. For example, the dentist can fixedly position the forehead support 17 against the patient's forehead or against the upper part of the patient's nose (e.g., below the nasion) (operation block 908). The patient's head is thus oriented and/or fixed at the correct position and orientation of the Frankfort plane (e.g., parallel to the x-ray source and cephalometric sensor plane) for cephalometric imaging using the visual indicator 30. At this point, a cephalometric scan of the imaging area (e.g., part or all of the skull) can be performed as known to one of ordinary skill in the art of cephalometric imaging (operation block 910).

In certain exemplary embodiments, the first patient positioning and holding system 6 can include a substantially transparent shield suspended from the mount 2 or the rotatable gantry 3, and a chin positioning element that can include a chin rest and a bite element. In one embodiment, the shield can include an open window disposed between a chin support and a forehead support. In one embodiment, the shield can be visibly transparent, transparent to additional radiation including x-rays and/or formed from a molded polycarbonate material. In one embodiment, the chin support can include a height adjuster for the bite element and the forehead support is configured to be adjustably pivotable toward the patient. In one embodiment, the shield can include one or more controls for setting a column height adjustment for the mount on the shield or mounted on a separate panel that is coupled to the shield. In one embodiment, the shield can include one or more markings to assist in patient positioning. In one embodiment, the shield can include a first Frankfort plane positioning indicator.

In certain exemplary embodiments, an extra-oral imaging system can include a support base adjustable in at least one dimension; a first mount mounted to the support base and configured to revolve an x-ray source and an imaging sensor panel about an imaging area; and a first patient positioning unit coupled to the extra-oral imaging system and positioned between the x-ray source and first sensor so that x-rays impinge the first sensor after radiating the imaging area, including a chin support coupled to the first patient positioning unit and includes a chin positioning element; a head support coupled to the first patient positioning unit shield; and a first Frankfort plan positioning indicator; a second mount mounted to the support base and configured to position a second imaging sensor panel about a second imaging area; and a second patient positioning unit coupled to the second mount and positioned between the x-ray source and the second sensor so that x-rays impinge the second sensor after radiating a second imaging area including a head support coupled to the second patient positioning unit; and a second Frankfort plane positioning indicator. In one embodiment, the second Frankfort plane positioning indicator is fixedly mounted, detachably mounted, or mounted to move between at least two positions, or rotatably mounted. In one embodiment, the second patient positioning unit is configured to repeatably and accurately position a patient between the x-ray source and the second imaging sensor panel. In one embodiment, an alignment indicator can include a elongated indicator, a solid line, a discontinuous indicator, a plurality of regularly spaced marks indicating a line, a plurality of irregularly spaced marks indicating a line, a partially transparent indicator, or the like, or a combination thereof.

In certain exemplary embodiments, a method for positioning a patient for extra-oral imaging can include revolving an x-ray source and an imaging sensor panel about a first imaging area; positioning a second imaging sensor panel for a second imaging area formed with the x-ray source; providing a second patient positioning unit positioned between the x-ray source and the second sensor so that x-rays impinge the second sensor after radiating the second imaging area; positioning a head support to indicate a first portion of the second imaging area; and reciprocally moving a second Frankfort plane positioning indicator between a first position aligning a marking on the second Frankfort plane positioning indicator between a second portion of the second imaging area and the first portion of the imaging area, and a second retracted position not aligning a marking on the second Frankfort plane positioning indicator between a second portion of the second imaging area. In one embodiment, the second retracted position is outside the second imaging area. In one embodiment, the second cephalometric Frankfort plane positioning indicator is configured to be mounted to one or both sides of the a collimator, at the second sensor imaging panel, at the at least one temporal holder, at a patient holder and/or the second mount or a portion of the second mount (e.g., cephalometric module). In at least one exemplary embodiment, a visual indicator can be transparent to x-ray radiation needed for some or all dental imaging modalities. In one embodiment, a cephalometric Frankfort plane positioning indicator can reciprocally move between at least 3 positions and can include a partially transparent visual plate and at least one horizontal indicator, where the at least one horizontal indicator can be aligned with a forehead support that indicates a bottom of the eye-ball socket and aligned with at least one ear rod in a cephalometric imaging area.

Consistent with exemplary embodiments of the application, a computer program utilizes stored instructions that perform on image data that is accessed from an electronic memory. As can be appreciated by those skilled in the image processing arts, a computer program for operating the imaging system in an exemplary embodiment of the present application can be utilized by a suitable, general-purpose computer system, such as a personal computer or workstation. However, many other types of computer systems can be used to execute the computer program of the present application, including an arrangement of networked processors, for example. The computer program for performing exemplary methods/apparatus of the present application may be stored in a computer readable storage medium. This medium may comprise, for example; magnetic storage media such as a magnetic disk such as a hard drive or removable device or magnetic tape; optical storage media such as an optical disc, optical tape, or machine readable optical encoding; solid state electronic storage devices such as random access memory (RAM), or read only memory (ROM); or any other physical device or medium employed to store a computer program. The computer program for performing exemplary methods/apparatus of the present application may also be stored on computer readable storage medium that is connected to the image processor by way of the internet or other network or communication medium. Those skilled in the art will further readily recognize that the equivalent of such a computer program product may also be constructed in hardware.

It should be noted that the term "memory", equivalent to "computer-accessible memory" in the context of the present disclosure, can refer to any type of temporary or more enduring data storage workspace used for storing and operating upon image data and accessible to a computer system, including a database, for example. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer is also considered to be a type of memory, as the term is used in the present disclosure. Memory is also used as the data workspace for executing and storing intermediate and final results of calculations and other processing. Computer-accessible memory can be volatile, non-volatile, or a hybrid combination of volatile and non-volatile types.

It will be understood that the computer program product of the present application may make use of various image manipulation algorithms and processes that are well known. It will be further understood that the computer program product embodiment of the present application may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product of the present application, are not specifically shown or described herein and may be selected from such algorithms, systems, hardware, components and elements known in the art.

The invention has been described in detail, and may have been described with particular reference to an exemplary or presently preferred embodiment, but it will be understood that variations and modifications can be effected within the spirit and scope of the invention. For example, exemplary visual indicator embodiments can be detachable (e.g., after alignment and before scanning) in contrast to moving to a retracted position. In one embodiment, a retracted position is a detached position. Also, a exemplary visual indicator embodiments can be mounted to different portions such a nasion with an indicator to then visually align (e.g., by the dentist) to a ear canal and/or an ear rod. Alternatively, exemplary visual indicator embodiments can be electronically detectable as transceivers mounted to alignment mechanisms (e.g., ear rods and a position verification part of a forehead support) that are initially positioned by the dentist relative to the patient, and then can be detected by remote sensors (e.g., transceivers) for confirmation or adjustment of the initial position, displayed (e.g., local at the apparatus or remote at a console), for repeatability and accuracy of this exam or between exams or the like. The presently disclosed exemplary embodiments are therefore considered in all respects to be illustrative and not restrictive. The scope of the invention is indicated by the appended claims, and all changes that come within the meaning and range of equivalents thereof are intended to be embraced therein.

Exemplary embodiments according to the application can include various features described herein (individually or in combination).

While the invention has been illustrated with respect to one or more implementations, alterations and/or modifications can be made to the illustrated examples without departing from the spirit and scope of the appended claims. In addition, while a particular feature of the invention can have been disclosed with respect to one of several implementations, such feature can be combined with one or more other features of the other implementations as can be desired and advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only, with a true scope and spirit of the invention being indicated by the following claims, and all changes that come within the meaning and range of equivalents thereof are intended to be embraced therein.

The invention claimed is:

1. An extra-oral imaging system, the extra-oral imaging system comprising:
   a support base adjustable in at least one dimension;
   a cephalometric module coupled to the support base and configured to position a cephalometric imaging sensor about a first imaging area formed with an x-ray source, where x-rays from the x-ray source impinge the cephalometric imaging sensor after radiating the first imaging area, the cephalometric module including a cephalometric imaging collimator;
   a cephalometric patient positioning unit positioned operatively near the first imaging area; and
   a retractable cephalometric Frankfort plane positioning indicator mounted to the cephalometric imaging collimator.

2. The extra-oral imaging system of claim 1, where the cephalometric patient positioning unit is between the cephalometric imaging collimator and the cephalometric sensor, and where the retractable cephalometric Frankfort plane positioning indicator is configured to reciprocally move between a first position closer to the first imaging area and a second retracted position that is spaced further away from the first imaging area.

3. The extra-oral imaging system of claim 1, where the cephalometric patient positioning unit is between the cephalometric imaging collimator and the cephalometric sensor, and where the cephalometric Frankfort plane positioning indicator is configured to reciprocally move between a first position where the cephalometric Frankfort plane positioning indicator is used to properly position a patient for cephalometric imaging and a retracted second position that is outside an x-ray beam path that impinges the cephalometric imaging sensor.

4. The extra-oral imaging system of claim 1, where the cephalometric patient positioning unit comprises:
   a head support coupled to the cephalometric patient positioning unit; and
   a positioning unit coupled to the cephalometric patient positioning unit, where the cephalometric Frankfort plane positioning indicator is rotatably mounted to the cephalometric imaging collimator or formed with a distal end longitudinally spaced from a mounted end, where the distal end is closer to the first imaging area.

5. The extra-oral imaging system of claim 1, where the cephalometric Frankfort plane positioning indicator comprises a partially transparent plate and at least one horizontal indicator.

6. The extra-oral imaging system of claim 1, where the cephalometric patient positioning unit is between the cephalometric imaging collimator and the cephalometric imaging sensor, and where the cephalometric patient positioning unit comprises:
   a forehead support, the forehead support being adjustable in at least two dimensions; and
   where the cephalometric Frankfort plane positioning indicator comprises a partially transparent plate and at least one horizontal indicator, where the at least one horizontal indicator is aligned with the forehead support that indicates a bottom of the eye-ball socket and is aligned with at least one ear rod in the first imaging area.

7. The extra-oral imaging system of claim 1, where the cephalometric patient positioning unit comprises at least one temporal holding member, where the cephalometric Frankfort plane positioning indicator comprises a partially transparent plate and at least one planar indicator, and where the at least one planar indicator can visually correspond to the at least one temporal holding member in the first imaging area.

8. The extra-oral imaging system of claim 1, where the cephalometric Frankfort plane positioning indicator is configured to be mounted to one or both sides of the cephalometric imaging collimator.

9. The extra-oral imaging system of claim 1, where the cephalometric patient positioning unit comprises at least one temporal holding member, and where the cephalometric Frankfort plane positioning indicator includes a thin shaft mounted in a first position to visually correspond to a temporal holding member in the first imaging area, where the cephalometric Frankfort plane positioning indicator is movably mounted to move into a position within a peripheral contour of the cephalometric imaging collimator or a portion of the cephalometric module.

10. The extra-oral imaging system of claim 1, where the cephalometric Frankfort plane positioning indicator comprises an elongated substantially transparent member with a mounting end and a distal end spaced from the mounting end, where the distal end comprises an alignment indicator, where the cephalometric Frankfort plane positioning indicator is mounted to reciprocally move between a first position where the alignment indicator proximate to the distal end visually corresponds to a temporal holding member and a second position where the alignment indicator is spaced apart and does not visually correspond to the temporal holding member.

11. The extra-oral imaging system of claim 1, where the cephalometric patient positioning unit is configured to position a patient in the first imaging area at a prescribed position where a Frankfort plane is not horizontal, and the cephalometric Frankfort plane positioning indicator is configured to indicate the prescribed position.

12. The extra-oral imaging system of claim 1, where the cephalometric patient positioning unit is configured to repeatably and accurately position a patient between the x-ray source and the cephalometric imaging sensor.

13. The extra-oral imaging system of claim 1, where the cephalometric Frankfort plane positioning indicator comprises a first Frankfort plane positioning indicator, and where the extra-oral imaging system further comprises:
   a mount mounted to the support base and configured to revolve the x-ray source and an imaging sensor separate from the cephalometric imaging sensor about a second imaging area so that x-rays impinge the imaging sensor after radiating the second imaging area; and a second patient positioning unit coupled to the extra-oral imaging system and positioned operatively near the second imaging area, comprising:
an elongated shield comprising handles;
a chin support coupled to the elongated shield and comprising a chin positioning element; and
a head support coupled to the elongated shield; and
a second Frankfort plane positioning indicator.

14. The extra-oral imaging system of claim 1, where the cephalometric Frankfort plane positioning indicator comprises at least one alignment indicator, where the alignment indicator comprises an elongated indicator, a solid line, a discontinuous indicator, a plurality of regularly spaced marks indicating a line, a plurality of irregularly spaced marks indicating a line, a partially transparent indicator, or a combination thereof.

15. The extra-oral imaging system of claim 1, where the cephalometric Frankfort plane positioning indicator is detachable and configured to mount to a plurality of positions having a prescribed spatial relationship to the first imaging area.

* * * * *